United States Patent
Medlin et al.

(10) Patent No.: US 6,945,448 B2
(45) Date of Patent: Sep. 20, 2005

(54) METHOD FOR ATTACHING A POROUS METAL LAYER TO A METAL SUBSTRATE

(75) Inventors: Dana J. Medlin, Warsaw, IN (US); Steven J. Charlebois, Goshen, IN (US); William Clarke, Warsaw, IN (US); Dirk L. Pletcher, Walkerton, IN (US); Joel G. Scrafton, Leesburg, IN (US); H. Ravindranath Shetty, Warsaw, IN (US); Dale Swarts, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/455,846

(22) Filed: Jun. 6, 2003

(65) Prior Publication Data

US 2003/0232124 A1 Dec. 18, 2003

Related U.S. Application Data

(60) Provisional application No. 60/389,615, filed on Jun. 18, 2002.

(51) Int. Cl.$^7$ ......................... B23K 31/00; B23K 31/02; B23K 35/12; B23K 1/19
(52) U.S. Cl. ................... 228/248.1; 228/253; 228/249; 228/262.3
(58) Field of Search .................... 228/248.1, 245, 228/253, 255, 249, 260, 261, 262.3, 262.31, 262.71, 262.72; 623/923, 920, 901; 427/2.24, 2.26, 455, 456, 475, 528, 531, 123, 124, 421, 427, 430.1, 431, 432, 435, 436

(56) References Cited

U.S. PATENT DOCUMENTS

| | | | | |
|---|---|---|---|---|
| 2,945,295 A | * | 7/1960 | Feaster | 228/220 |
| 3,353,259 A | * | 11/1967 | Kirkpatrick | 228/208 |
| 3,605,123 A | * | 9/1971 | Hanh | 623/23.55 |
| 3,855,638 A | * | 12/1974 | Pilliar | 623/23.55 |
| 3,906,550 A | * | 9/1975 | Rostoker et al. | 623/23.55 |
| 4,570,271 A | * | 2/1986 | Sump | 128/898 |
| 4,612,160 A | * | 9/1986 | Donlevy et al. | 419/2 |
| 4,636,219 A | * | 1/1987 | Pratt et al. | 623/23.3 |
| 4,644,942 A | * | 2/1987 | Sump | 623/23.55 |
| 5,080,672 A | * | 1/1992 | Bellis | 427/2.1 |
| 5,104,410 A | * | 4/1992 | Chowdhary | 623/11.11 |
| 5,192,324 A | * | 3/1993 | Kenna | 623/23.55 |
| 5,198,308 A | * | 3/1993 | Shetty et al. | 428/608 |
| 5,282,861 A | * | 2/1994 | Kaplan | 623/23.51 |
| 5,323,954 A | * | 6/1994 | Shetty et al. | 228/187 |
| 5,358,527 A | * | 10/1994 | Forte | 623/20.27 |
| 5,441,537 A | * | 8/1995 | Kenna | 419/2 |
| 5,504,300 A | * | 4/1996 | Devanathan et al. | 219/121.64 |
| 5,734,959 A | * | 3/1998 | Krebs et al. | 419/2 |
| 5,773,789 A | * | 6/1998 | Devanathan et al. | 219/121.64 |
| 5,800,552 A | * | 9/1998 | Forte | 623/20.27 |
| 5,926,685 A | * | 7/1999 | Krebs et al. | 419/2 |
| 6,470,568 B2 | * | 10/2002 | Fried et al. | 29/889.1 |
| 6,544,472 B1 | * | 4/2003 | Compton et al. | 419/2 |
| 6,708,869 B2 | * | 3/2004 | Hyogo et al. | 228/183 |

FOREIGN PATENT DOCUMENTS

| | | | | |
|---|---|---|---|---|
| JP | 355045505 A | * | 3/1980 | |
| JP | 200353523 A | * | 2/2003 | |

* cited by examiner

*Primary Examiner*—Colleen P. Cooke
(74) *Attorney, Agent, or Firm*—Johathan Feuchtwang; Zimmer Technology, Inc.

(57) ABSTRACT

A method for attaching a porous metal layer to a dense metal substrate, wherein the method is particularly useful in forming orthopedic implants such as femoral knee components or acetabular cups. The method, in one embodiment thereof, comprises providing a structured porous layer; providing a dense metal substrate; providing a binding mixture; applying the binding mixture to the exterior of the substrate; placing the porous layer against the substrate such that the binding mixture is disposed there between forming an assembly; and heat treating the assembly to metallurgically bond the porous layer to the substrate.

23 Claims, 3 Drawing Sheets

METHOD FOR ATTACHING A POROUS METAL LAYER TO A METAL SUBSTRATE

This application is a non-provisional patent application that claims the benefit of U.S. provisional patent application No. 60/389,615 filed Jun. 18, 2002.

BACKGROUND OF THE INVENTION

1. Field of the Invention

The present invention relates to orthopedic implants of the type having a porous surface into which bone tissue can grow or bone cement can enter and, more particularly, to a method of bonding a porous metal structure, such as porous titanium or porous tantalum onto a metal substrate preferably comprising a titanium-based or cobalt-based alloy.

2. Description of the Related Art

Orthopedic implant devices commonly include a porous structure of desired thickness, generally 0.5 to 5.0 mm, on the bone contacting surface of the implant to promote bone growth there through and to enhance attachment of the device to adjacent bone tissue. Growth of bone into an implant is advantageous in that the same allows for increased fixation of the implant.

Accordingly, it is desirable to promote as much bone growth into an implant as possible. Various methods have been developed for manufacturing an orthopaedic implant device having a porous surface, including plasma spraying of metal powder, sintering of metal beads, and diffusion bonding of metal wire mesh. See for example, the following patents, the disclosures of which are hereby incorporated by reference and briefly described herein.

U.S. Pat. No. 3,906,550 to Rostoker et al. discloses a porous metal structure adapted for attachment to a prosthesis. The fiber metal is molded into the desired shape using dies. The fiber metal is then sintered together to form metallurgical bonds within the pad and between fiber metal pad and the substrate.

U.S. Pat. No. 3,605,123 to Hahn discloses a metallic bone implant having a porous metallic surface layer. The porous layer may be secured to the implant by a plasma spray method or by other suitable means.

U.S. Pat. No. 4,636,219 to Pratt et al. discloses a prosthesis including a porous surface comprised of a layered metal mesh structure and a process for fabricating the mesh screen structure for bonding to the prosthesis. The mesh may be bonded to a thin substrate which can then be cut or formed and applied to the body of a prosthesis on a flat surface or contoured into specific shapes by forming.

U.S. Pat. No. 4,570,271 to Sump discloses a prosthesis with a porous coating in which the porous coating is preformed directly into the desired shape which corresponds to the preselected surface of the prosthesis. The preformed porous coating is then overlaid onto the preselected surface, compressed, and heated to adhere the preformed porous coating to the prosthesis.

U.S. Pat. No. 3,855,638 to Pilliar described the bonding process to a prosthetic device having a solid metallic substrate with a porous coating adhered thereto. A slurry of metallic particles was applied to the substrate, dried and then sintered to establish metallurgical bond between particles and the substrate.

U.S. Pat. Nos. 5,198,308 and 5,323954 entitled "Titanium Porous Surface Bonded to a Cobalt-Based Alloy Substrate in Orthopaedic Implant Device and Method of Bonding Titanium to a Cobalt-Based Alloy Substrate in an Orthopaedic Implant Device" which are assigned to assignee of the present invention teaches diffusion bonding of titanium fiber metal pad porous layer to Co—Cr—Mo alloy implants with the use of a thin titanium and or L-605 alloy foil to increase the bond strength of the coating to the substrate and corrosion resistance of the implant.

U.S. Pat. No. 5,104,410 granted to Chowdhary discloses the method of making a surgical prosthetic device, comprising of a composite structure having a solid metal substrate and a porous coating with multiple sintered layers. The porous coating has an external layer to accept bone ingrowth and the chemical composition of the external layer is same as the intermediate layer between the porous coating and the implant surface. The intermediate layer bonds the external porous layer to the substrate. These layers are applied in a process of multiple sintering where each successive layer is individually sintered to the substrate or the proceeding layer, as applicable. This process provides a porous layer having increased strength of attachment between the substrate and the external porous layer.

Titanium is a known biocompatible metal that is often used in orthopedic applications. Porous titanium or porous titanium alloy can be used on the bone contacting surface of an orthopedic implant to promote bone growth there through. Tantalum is another known biomaterial. Tantalum is known to be particularly adept at promoting bone growth. Implex, Inc. markets a structured porous tantalum metal biomaterial, described in U.S. Pat. No. 5,282,861, for orthopedic use under the trade name HEDROCEL®. HEDROCEL is described as being more than 80% porous, and closely resembles human trabecular bone in both physical and mechanical properties. In spite of the value of using a porous layer in orthopedic implants, bonding porous metal to a metal substrate such as cobalt alloy or titanium alloy has been difficult, especially in the case of HEDROCEL. The reason for this difficulty is that metallurgically bonding two components generally requires a large amount of contact between the surfaces at which the bond is desired. The porosity of HEDROCEL results in sparse contact with an opposing metal substrate, thereby making sintering or diffusion bonding difficult. Moreover, this porosity also makes it difficult to maintain the narrow dimensioning tolerances for machined HEDROCEL, components. The binding mixture, therefore, also serves to fill in "gaps" or "spaces" that may exist between a HEDROCEL porous layer of desired shape and a corresponding metal substrate.

Thus, a need exists for a method of bonding a porous metal structure to a metal substrate.

An additional need exists for a method of bonding a porous metal surface to a component of an orthopedic implant device comprising a solid metal, such as cobalt-chrome alloy or titanium alloy.

SUMMARY OF THE INVENTION

The present invention provides a method of bonding a porous metal layer, comprising for example, HEDROCEL, to a titanium alloy or cobalt alloy substrate. More specifically, the bonding process of the present invention involves bonding a porous metal layer directly onto titanium alloy or cobalt alloy surfaces using a sintering or diffusion bonding process that includes a means for producing good surface contact between the porous metal and the substrate.

In one embodiment, the method of the present invention comprises: providing a metal substrate; providing a binding mixture; providing a porous metal structure; applying the mixture to the substrate or to the porous metal; placing the porous metal structure against the substrate such that the binding mixture is disposed between the porous metal and the substrate, thereby forming an assembly; and subjecting the assembly to heat and/or pressure thereby metallurgically bonding the porous metal to the substrate. In this first embodiment, the binding mixture is used to provide contact between the porous metal and the substrate.

In a another embodiment, the method of the present invention comprises: providing a metal substrate; providing the porous metal structure; "contouring" the surface of (as defined subsequently herein) of the porous metal structure; placing the porous metal structure against the substrate, thereby forming an assembly; and subjecting the structure to heat and/or pressure to metallurgically bond the porous metal structure to the substrate. In this second embodiment, surface contact between the porous metal structure and the substrate is achieved by contouring the surface of the porous metal prior to placing it against the substrate.

The invention, in another form thereof, further provides a method of making an orthopedic implant having a porous metal layer bonded to a metal component of an implant.

An advantage of the bonding method of the present invention is that a porous metal structure can be bonded to titanium-based and cobalt-based alloy substrates.

A further advantage of the bonding method of the present invention is that a single bonding process is employed thereby protecting the metallurgical properties of the component alloys of the assembly.

Another advantage of the present invention is that orthopaedic implant devices produced according to the present invention comprise a porous metal surface provided on titanium-based and cobalt-based alloy substrates with enhanced bond strength and corrosion resistance.

Other advantages of the present invention will be apparent to those of skill in the art upon reviewing the appended specification, drawings, and claims.

BRIEF DESCRIPTION OF THE DRAWINGS

The above-mentioned and other features and objects of this invention, and the manner of obtaining them, will become more apparent and the invention itself will be better understood by reference to the following description of an embodiment of the invention taken in conjunction with the accompanying drawings and claims, wherein:

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
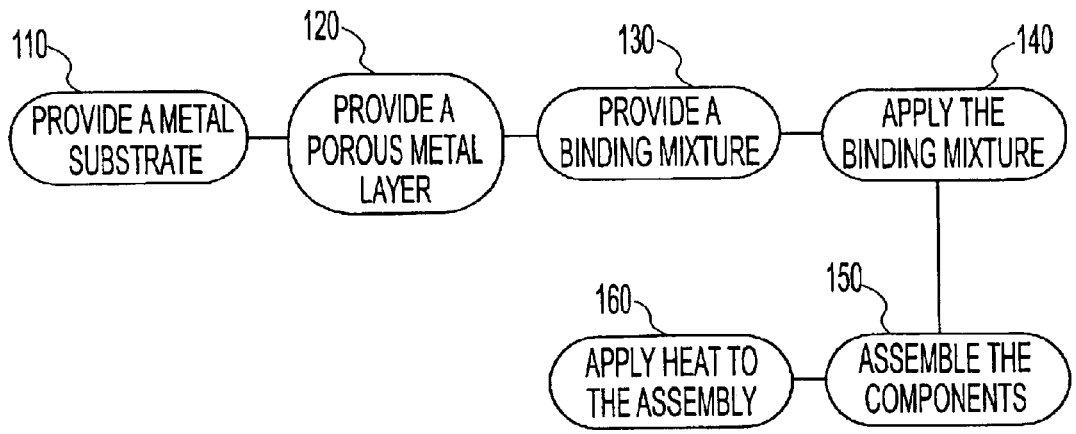
FIG. 1 is a diagrammatic view of a first embodiment of the present invention.

Referring now to FIG. 1, there is shown a diagrammatic view of a first embodiment of the present invention.

Figure 4:
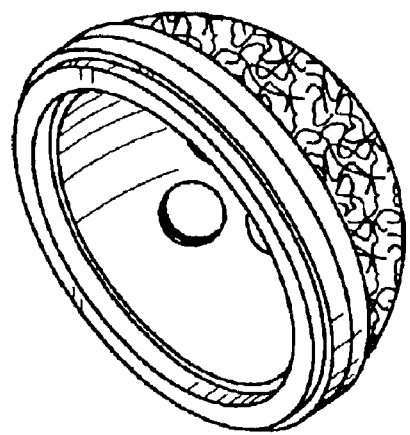
FIG. 4 is a perspective view of the femoral component of an endoprosthetic knee joint constructed according to the present invention.
Figure 5:
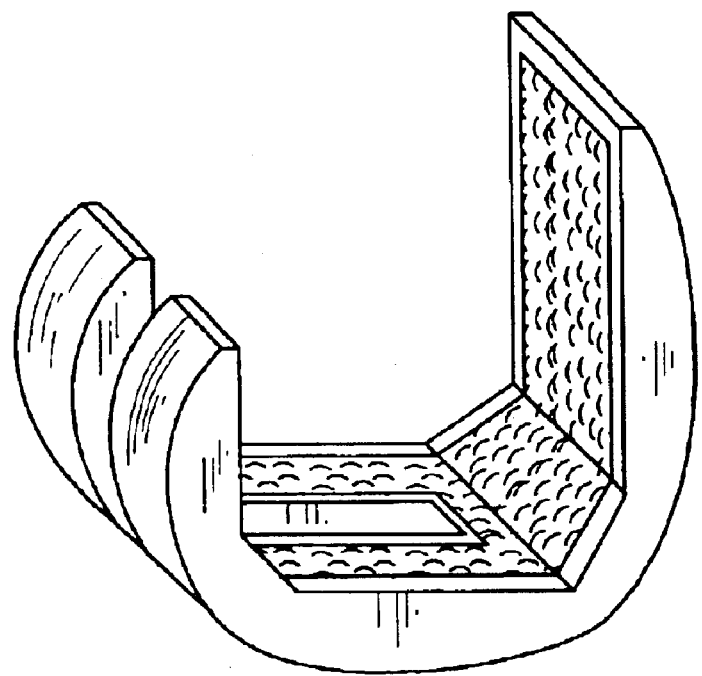
FIG. 5 is a perspective view an acetabular cup constructed according to the present invention.

Generally, Block 110 represents providing a metal substrate. In the present invention, the term "metal substrate" refers to titanium based or cobalt based alloys as are often used in orthopedic applications. Titanium alloys such as Ti-6Al-4V alloy or Ti-6Al-7Nb alloy having a rating of ASTM F-136 or F-1295 respectively are preferred. Cobalt based alloys, specifically cast Co—Cr—Mo alloy or wrought Co—Cr—Mo alloy, having an ASTM designation of F-75 or F-1537 respectively, may also be used. In some instances, it is desirable to use a cobalt based alloy having a layer of commercially pure titanium or titanium alloy plasma sprayed thereon. The above stated metals are preferred because of their strength, corrosion resistance and biocompatibility. In the orthopedic applications for which the method of the present invention will most commonly, although not exclusively, be used, the metal substrate will be shaped in a manner desirable to function as a component of an orthopedic implant, for example, an acetabular cup as shown in FIG. 5 of the present invention or a femoral component for an endoprosthetic knee as shown in FIG. 4 of the present invention. However, those skilled in the art will appreciate that the present invention is applicable to any application wherein one desires to metallurgically bond a porous metal layer to a metal substrate.

Referring still to FIG. 1, there is shown Block 120 which represents providing a porous metal layer. In a preferred embodiment, a porous tantalum structure is used. The porous metal layer is preferably provided in a desired shape suitable for a particular application. For example, a hemispherical shape may be used as a shell for an acetabular cup orthopedic implant. The porous metal layer may also be provided as a pad for use on the bone contacting surface of a standard femoral component for an orthopedic knee implant.

In order to provide a strong metallurgical bond (i.e. a pull apart strength of at or above about 2900 p.s.i.) between the metal substrate and porous metal layer via sintering or diffusion bonding, there must be sufficient surface contact between the components. Those skilled in the art will appreciate that, on a microscopic level, neither the surface of the metal substrate, nor the surface of the porous metal layer is perfectly contoured. Thus, a less than critical amount of surface contact for producing a metallurgical bond will exist between a porous metal layer and a metal substrate disposed directly against one another, unless a means of producing sufficient surface contact is provided. In addition, the fact that narrow tolerance ranges are difficult to obtain for machined shapes comprising porous metal structures, such as HEDROCEL, makes it likely that one will find gaps between the adjacent surfaces of a porous layer placed against a metal substrate.

One preferred means of ensuring that sufficient surface contact is present is to provide a binding mixture between the substrate and porous layer. The binding mixture fills in the porous surface of the porous tantalum layer thereby "contouring" the surface, and it fills in the "gaps" between the porous layer and the substrate, thereby providing sufficient surface contact for metallurgically bonding the porous tantalum layer and the metal substrate.

Thus, referring again to FIG. 1, there is shown a Block 130 which represents providing a binding mixture. Generally, the binding mixture of the present invention comprises an organic binder with sufficient adhesive strength to hold a metal powder in place. It is preferable to choose an organic binder that decomposes within the temperate range of the diffusion bonding or sintering step discussed subsequently herein. The organic binder may be selected from the group consisting of gelatin, glycerin, polyvinyl alcohol ("PVA") or a combination of the same. The binding mixture further comprises powdered metal wherein the metal is preferably the same as the metal used to form the metal substrate. However, different metals that have good mutual solubility between the substrate and the material comprising the porous layer may be used in the binding mixture. For example, cobalt-chrome alloy, hafnium, manganese, niobium, palladium, titanium-6, aluminum-4, vanadium alloy, aluminum-7, titanium-nickel alloy, zirconium, zirconium alloys, Ti-6Al-4V, Ti-6Al-7Nb, commercially pure titanium, titanium alloys, and cobalt-chromium-molybdenum.

The binding mixture preferably comprises about 68% by volume powdered metal and about 32% by volume of a solution comprising 10% PVA and 90% water. However the binding mixture may comprise between above about 10% by volume powdered metal and about 95% by volume powdered metal. Exemplary binding mixture configurations are shown in the EXAMPLES section of this application.

Referring still to FIG. 1 there is shown in Block 140, representing the step of applying the binding mixture to the porous layer. In the preferred embodiment, the binding mixture is applied to the porous layer, and for clarity of explanation, the present invention is described as having the binding mixture applied to the porous layer. However, it is to be appreciated that the binding mixture can also be applied to the substrate, depending on the shape of the components that one desires to bond and the viscosity of a chosen binding mixture. In any event, it is desirable to apply the binding mixture as evenly as possible. Preferably, the binding mixture is sprayed onto the porous layer, but the porous layer may also be dipped into the binding mixture, or the binding mixture may be painted on porous layer. Alternatively, the same techniques may be used to apply the binding mixture to the substrate. An example of a technique for applying a binding mixture is illustrated in U.S. Pat. No. 5,198,308, assigned to the assignee of the present application, and whose subject matter is hereby incorporated by reference into the present application.

Referring again to FIG. 1, there is shown Block 150, which represents the step of assembling the substrate and the porous metal layer such that the binding mixture is disposed therebetween. This step may be accomplished by any desirable means known in the art whereby a first component is placed against a second component.

Referring again to FIG. 1 there is shown in Block 160, which represents the step of heating the assembly, to complete the bonding process. In a preferred embodiment, the heating step comprises: heating the assembly in a debinding cycle to a temperature of within about 100° C. to about 600° C. preferably in an inert atmosphere consisting essentially of argon or helium having at most trace amounts of oxygen or nitrogen. Alternatively, the heating step may be conducted in a partial vacuum environment having a pressure of 0.01 torr or less. The assembly is held at this temperature for about 1 hour to about 4 hours to remove the organic binder contained in the binding mixture. A sintering cycle is then run at about 800° C. to 1600° C. for about 1 to 4 hours.

Figure 2:
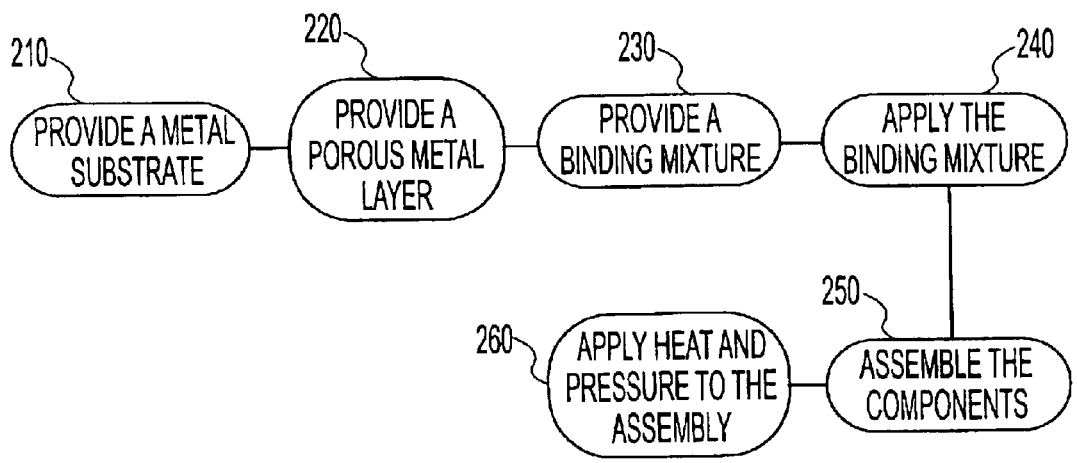
FIG. 2 is a diagrammatic view of a second embodiment of the present invention.

Referring now to FIG. 2, there is shown an alternative embodiment of the present invention, comprising the steps of providing a metal substrate, Block 210; providing a porous tantalum layer, Block 220; providing a binding mixture, Block 230; applying the binding mixture to the substrate, Block 240; assembling the parts, Block 250; and applying heat and pressure to the assembly, Block 260.

In the alternative embodiment shown in FIG. 2, the steps are largely as described above; however, the step of applying heat and pressure, shown in Block 260, comprises: heating the assembly to within a temperature of within about 100° C. to about 600° C., preferably in an inert or partial vacuum environment, and under a clamping pressure of between 200 and 1200 p.s.i. The clamping pressure is useful in assuring suitable surface contact between the substrate and porous layer. Also, the heating temperature required to achieve a particular bond strength between the porous component and substrate is generally inversely proportional to the amount of clamping pressure used. The assembly is held at the desired temperature and pressure for about 1 hour to about 4 hours.

Figure 3:
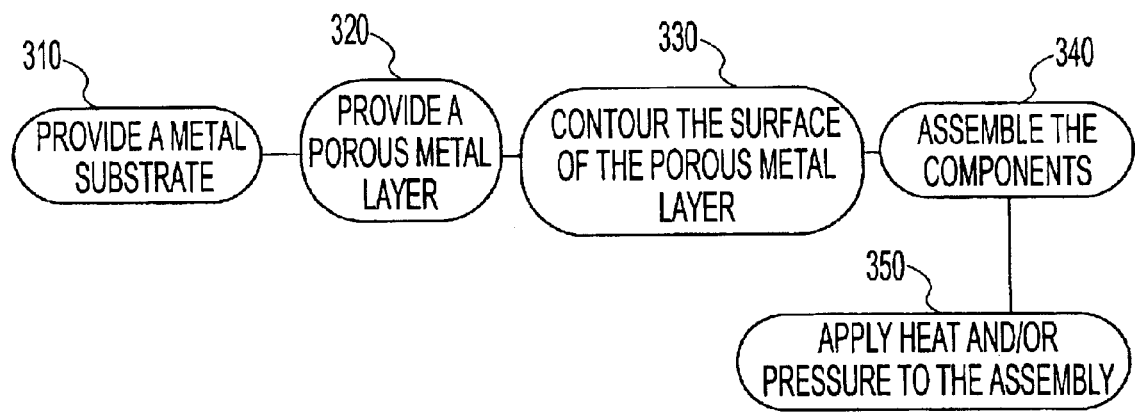
FIG. 3 is a diagrammatic view of a third embodiment of the present invention.

In FIG. 3, there is shown another embodiment of the present invention comprising the steps of: providing a metal substrate, Block 310 providing a porous tantalum layer, Block 320 contouring the surface of the porous metal layer, Block 330 assembling the parts, Block 340 and applying heat and/or pressure to the assembly, Block 350.

In the embodiment of FIG. 3, the steps of providing a metal substrate, Block 310 and providing a tantalum porous layer, Block 320 are the same as described previously herein with regard to the embodiment of FIG. 1. However, in this third embodiment of the present invention, no binding mixture is used to enable the porous tantalum layer to have adequate surface contact with the substrate. Instead, an alternative means is used to contour the porous tantalum layer to ensure that sufficient surface contact exists between the components of the assembly. Specifically, as represented by Block 330, the surface of the porous layer is mechanically contoured or smeared to provide more surface contact with the substrate. Generally, machining methods well known in the art are used to contour the surface of the porous tantalum layer a desirable amount. Alternatively, electro discharge machining may be used to contour the surface of the porous tantalum layer.

Referring still to FIG. 3, the substrate and porous layer are assembled as shown in Block 340, and heat and/or pressure are applied to the assembly as shown in Block 350. The step of Block 350 comprises: heating the assembly to within a temperature of within about 800° C. to about 1600° C. in a low oxygen or partial vacuum environment. A clamping pressure may be used if desired. The assembly is held at this temperature and pressure for about 1 hour to about 4 hours.

Those skilled in the art will appreciate that for each embodiment of the invention the times, temperatures, and pressures may be manipulated to vary the bond strength between the porous layer and the substrate and to vary the effects of the process on the mechanical properties of the porous layer and the substrate. In addition, the multiple cycles of applying heat and/or pressure may used to similarly affect the strength of bond between components or the mechanical properties of the substrate or porous layer.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims or their equivalents.

EXAMPLES

| SUBSTRATE MATERIAL | POROUS LAYER | CYCLE TEMPERATURE | CYCLE TIME | ENVIRONMENT | CLAMPING PRESSURE | BINDING MIXTURE |
|---|---|---|---|---|---|---|
| Ti-6 AL—V | HEDROCEL | 955° C. | 2 cycles at 4 hours each | Argon | 400 p.s.i. | 68% PVA + 32% (10% PVA, 90% water solution) |
| Ti-6 AL—V | HEDROCEL | 955° C. | 2 cycles at 4 hours each | Helium | 400 p.s.i. | 68% PVA + 32% (10% PVA, 90% water solution) |
| Ti-6 AL—V | HEDROCEL | 955° C. | 2 cycles at 4 hours each | Argon | 400 p.s.i. | N/A |
| Ti-6 AL—V | Machined HEDROCEL | 350° C. (debind) + 1200° C. (sintering) | 3 hours (debind) + 4 hours (sintering) | 0.01 Torr | N/A | 68% PVA + 32% (10% water solution) |
| Co—Cr—Mo | Machined HEDROCEL | 1094° C. | 2 cycles at 4 hours each | 0.01 Torr | 400 p.s.i. | 68% PVA + 32% (10% PVA, 90% water solution) |

We claim:

1. A method for attaching a porous metal structure to a metal substrate, the method comprising:
   providing a metal substrate comprising a metal selected from the group consisting of cobalt, cobalt alloy, titanium and titanium alloy;
   providing a binding mixture;
   providing the porous metal structure;
   applying the binding mixture to the porous structure by means selected from the group consisting of spraying, and dipping; placing the porous structure against the substrate such that the binding mixture is disposed between the metal component and the porous structure, thereby forming an assembly; and
   heating the assembly to metallurgically bond the porous structure and the substrate.

2. The method of claim 1, wherein the binding mixture comprises a suspending additive selected from the group consisting of gelatin, PVA and water, and wherein the binding mixture further comprises a powdered metal.

3. The method of claim 2, wherein the metal powder is selected from the group consisting of cobalt, cobalt alloy, hafnium, molybdenum, palladium, niobium, zirconium, zirconium alloy, titanium, and titanium alloy.

4. The method of claim 3, wherein the binding mixture comprises above about 10% by volume powdered metal.

5. The method of claim 3, wherein the binding mixture comprises above about 30% by volume powder.

6. The method of claim 3, wherein the binding mixture comprises above about 68% by volume powdered metal.

7. The method of claim 3, wherein the binding mixture comprises about 95% by volume powdered metal.

8. The method of claim 1, wherein the heating step comprises:
   heating the assembly at about 100° C. to 600° C. for about 1 to 4 hours; and further heating the assembly at about 800° C. to 1600° C. for about 1 hour to about 4 hours.

9. The method of claim 8, wherein the heating step is performed in an inert environment comprising a gas selected from the group consisting of argon and helium.

10. The method of claim 8, wherein the heating step is performed in an at least partial vacuum.

11. A method for attaching a porous metal structure to a metal substrate, the method comprising:
   providing a metal substrate comprising a metal selected from the group consisting of cobalt, cobalt alloy, titanium and titanium alloy;
   providing a binding mixture;
   providing the porous metal structure; applying the binding mixture to the porous structure by means selected from the group consisting of spraying, and dipping;
   placing the porous structure against the substrate such that the binding mixture is disposed between the metal component and the porous structure, thereby forming an assembly; and
   applying heat and pressure to the assembly to metallurgically bond the porous structure and the substrate.

12. The method of claim 11, wherein the binding mixture comprises a suspending additive selected from the group consisting of gelatin, PVA and water, and wherein the binding mixture further comprises a powdered metal.

13. The method of claim 12, wherein the powdered metal is selected from the group consisting of cobalt, cobalt alloy, hafnium, molybdenum, palladium, niobium, zirconium, zirconium alloy, titanium, and titanium alloy.

14. The method of claim 13, wherein the binding mixture comprises above about 10% by volume powdered metal.

15. The method of claim 13, wherein the binding mixture comprises above about 30% by volume powdered metal.

16. The method of claim 13, wherein the binding mixture comprises above about 68% by volume powdered metal.

17. The method of claim 13, wherein the binding mixture comprises about 95% by volume powdered metal.

18. The method of claim 11, wherein the step of applying heat and pressure comprises: heating the assembly to about 800° C. to 1600° C. for about 1 hour to about 4 hours, at a clamping pressure of between about 200 p.s.i, and 1200 p.s.i.

19. The method of claim 18, wherein the step of applying heat and pressure is performed in an inert environment comprising a gas selected from the group consisting of argon and helium.

20. The method of claim 18, wherein the step of applying heat and pressure is performed in an at least partial vacuum.

21. A method for attaching a porous metal structure to a metal component of an orthopedic implant, the method comprising:

providing a metal component comprising a metal selected from the group consisting of cobalt, cobalt alloy, titanium and titanium alloy, said metal component having a desired shape and a bone contacting surface;

providing a binding mixture;

providing the porous metal structure in a desired shape;

applying the binding mixture to the porous structure by means selected from the group consisting of spraying, and dipping;

placing the porous structure against the bone contacting surface of the metal component such that the binding mixture is disposed between the metal component and the porous structure, thereby forming an assembly; and heating the assembly to metallurgically bond the porous structure and the metal component.

22. A method for attaching a porous metal structure to a metal component of an orthopedic implant, the method comprising:

providing a metal component comprising a metal selected from the group consisting of cobalt, cobalt alloy, titanium and titanium alloy, said metal component having a desired shape and a bone contacting surface;

providing a binding mixture;

providing the porous metal structure in a desired shape;

applying the binding mixture to the porous structure by means selected from the group consisting of spraying, and dipping;

placing the porous structure against the bone contacting surface of the metal component such that the binding mixture is disposed between the metal component and the porous metal structure, thereby forming an assembly; and applying heat and pressure to the assembly to metallurgically bond the porous structure and the metal component.

23. The method of any one of claims 1–20, 21 or 22, wherein the step of applying the binding mixture comprises applying the binding mixture to the metal substrate and to the porous metal layer.

* * * * *

UNITED STATES PATENT AND TRADEMARK OFFICE
CERTIFICATE OF CORRECTION

| | | |
|---|---|---|
| PATENT NO. | : 6,945,448 B2 | |
| APPLICATION NO. | : 10/455846 | |
| DATED | : September 20, 2005 | |
| INVENTOR(S) | : Dana J. Medlin et al. | |

It is certified that error appears in the above-identified patent and that said Letters Patent is hereby corrected as shown below:

In Column 7, in the Binding Mixture column of the table, change each occurrence of 68% PVA to read 68% powdered metal Signed and Sealed this
Eighteenth Day of October, 2011

David J. Kappos
*Director of the United States Patent and Trademark Office*